US012716073B2

(12) United States Patent
Mao et al.

(10) Patent No.: US 12,716,073 B2
(45) **Date of Patent: *Aug. 25, 2026**

(54) COMPOSITION OF SHELF-STABLE PLASMID DNA/POLYETHYLENEIMINE (PEI) PARTICLES WITH DEFINED SIZES FOR VIRAL VECTOR PRODUCTION AND METHOD FOR PREPARATION OF THE SAME

(71) Applicant: The John Hopkins University, Baltimore, MD (US)

(72) Inventors: Hai-Quan Mao, Baltimore, MD (US); Yining Zhu, Baltimore, MD (US); Yizong Hu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 561 days.

This patent is subject to a terminal disclaimer.

(21) Appl. No.: 18/546,222

(22) PCT Filed: Feb. 16, 2022

(86) PCT No.: PCT/US2022/016584

§ 371 (c)(1), (2) Date: Aug. 11, 2023

(87) PCT Pub. No.: WO2022/177981

PCT Pub. Date: Aug. 25, 2022

(65) Prior Publication Data

US 2024/0117376 A1 Apr. 11, 2024

Related U.S. Application Data

(60) Provisional application No. 63/149,983, filed on Feb. 16, 2021.

(51) Int. Cl.

| | |
|---|---|
| ***C12N 15/85*** | (2006.01) |
| ***C12N 5/071*** | (2010.01) |
| ***C12N 7/00*** | (2006.01) |
| *B82Y 5/00* | (2011.01) |

(52) U.S. Cl.

CPC .......... *C12N 15/85* (2013.01); *C12N 5/0686* (2013.01); *C12N 7/00* (2013.01); *B82Y 5/00* (2013.01); *C12N 2740/15051* (2013.01)

(58) Field of Classification Search

None

See application file for complete search history.

(56) References Cited

U.S. PATENT DOCUMENTS

| | | | |
|---|---|---|---|
| 2009/0233359 | A1 | 9/2009 | Kwon |
| 2010/0029750 | A1 | 2/2010 | Gupta et al. |
| 2010/0221346 | A1 | 9/2010 | Plank et al. |

FOREIGN PATENT DOCUMENTS

| | | | |
|---|---|---|---|
| CN | 109072252 | A | 12/2018 |
| CN | 111714643 | | 9/2020 |
| EP | 4294451 | A1 | 12/2023 |
| WO | WO 2011/127255 | | 10/2011 |
| WO | WO 2020/198015 | | 10/2020 |
| WO | WO 2020/223323 | | 11/2020 |

OTHER PUBLICATIONS

International Search Report and Written Opinion for PCT/US22/16584. Mailed May 23, 2022. 10 pages.

Bertschinger et al., A spectrophotometric assay for the quantification of polyethylenimine in DNA nanoparticles. Anal Biochem. Nov. 1, 2004;334(1):196-8.

Bertschinger et al., Disassembly of polyethylenimine-DNA particles in vitro: implications for polyethylenimine-mediated DNA delivery. J Control Release. Nov. 2006;116(1):96-104.

Bivas-Benita et al., PLGA-PEI nanoparticles for gene delivery to pulmonary epithelium. Eur J Pharm Biopharm. Jul. 2004;58(1):1-6.

Boussif et al., A versatile vector for gene and oligonucleotide transfer into cells in culture and in vivo: polyethylenimine. Proc Natl Acad Sci U S A. Aug. 1, 1995;92(16):7297-301.

Bus et al., The great escape: how cationic polyplexes overcome the endosomal barrier. J Mater Chem B. Nov. 21, 2018;6(43):6904-6918.

Curtis et al., Unusual Salt and pH Induced Changes in Polyethylenimine Solutions. PLoS One. Sep. 29, 2016;11(9):e0158147. 20 pages.

Dalby et al., Advanced transfection with Lipofectamine 2000 reagent: primary neurons, siRNA, and high-throughput applications. Methods. Jun. 2004;33(2):95-103.

Hao et al., Flow physics and mixing quality in a confined impinging jet mixer. AIP Adv. Apr. 2, 2020;10(4):045105. 10 pages.

Hu et al., Kinetic Control in Assembly of Plasmid DNA/Polycation Complex Nanoparticles. ACS Nano. Sep. 24, 2019;13(9):10161-10178.

Hu et al., Size-Controlled and Shelf-Stable DNA Particles for Production of Lentiviral Vectors. Nano Lett. Jul. 14, 2021;21(13):5697-5705.

Johnson et al., Chemical processing and micromixing in confined impinging jets. AIChE Journal, 2003, 49, 2264-2282.

Karlsson et al., Poly(beta-amino ester)s as gene delivery vehicles: challenges and opportunities. Expert Opin Drug Deliv. Oct. 2020;17(10):1395-1410.

Kilchrist et al., Gal8 Visualization of Endosome Disruption Predicts Carrier-Mediated Biologic Drug Intracellular Bioavailability. ACS Nano. Feb. 26, 2019;13(2):1136-1152.

(Continued)

*Primary Examiner* — Nannette Holloman

(74) *Attorney, Agent, or Firm* — Casimir Jones, SC; Jeffrey W. Childers

(57) ABSTRACT

A scalable method for producing DNA/polycation particles having an optimal, defined particle size with multiple virus assembly plasmids for efficient transfection of viral production cells in suspension cultures. The presently disclosed DNA/polycation particles yield superior and reproducible transfection activity and shelf stability in the suspension form and can be used as an off-the-shelf product. The presently disclosed DNA/polycation particle formulation can potentially simplify and streamline the viral manufacturing process and improve production quality and consistency.

16 Claims, 8 Drawing Sheets

(56) References Cited

OTHER PUBLICATIONS

Ko et al., Polyethylenimine/oligonucleotide polyplexes investigated by fluorescence resonance energy transfer and fluorescence anisotropy. Oligonucleotides. Mar.-Apr. 2011;21(2):109-14.
Kopatz et al., A model for non-viral gene delivery: through syndecan adhesion molecules and powered by actin. J Gene Med. Jul. 2004;6(7):769-76.
Lachelt et al., Nucleic Acid Therapeutics Using Polyplexes: A Journey of 50 Years (and Beyond). Chem Rev. Oct. 14, 2015;115(19):11043-78.
Lu et al., Chitosan-graft-polyethylenimine/DNA nanoparticles as novel non-viral gene delivery vectors targeting osteoarthritis. PLoS One. Jan. 2, 2014;9(1):e84703. 12 pages.
Mayor et al., Pathways of clathrin-independent endocytosis. Nat Rev Mol Cell Biol. Aug. 2007;8(8):603-12.
Merten et al., Production of lentiviral vectors. Mol Ther Methods Clin Dev. Apr. 13, 2016:3:16017. 14 pages.
Milone et al., Clinical use of lentiviral vectors. Leukemia. Jul. 2018;32(7):1529-1541.
Mislick et al., Evidence for the role of proteoglycans in cation-mediated gene transfer. Proc Natl Acad Sci U S A. Oct. 29, 1996;93(22):12349-54.
Ogris et al., The size of DNA/transferrin-PEI complexes is an important factor for gene expression in cultured cells. Gene Ther. Oct. 1998;5(10):1425-33.
Ohi et al., Negative Staining and Image Classification—Powerful Tools in Modern Electron Microscopy. Biol Proced Online. 2004:6:23-34.
Osada et al., Quantized folding of plasmid DNA condensed with block catiomer into characteristic rod structures promoting transgene efficacy. J Am Chem Soc. Sep. 8, 2010;132(35):12343-8.
Pear et al., Production of high-titer helper-free retroviruses by transient transfection. Proc Natl Acad Sci U S A. Sep. 15, 1993;90(18):8392-6.
Pollard et al., Polyethylenimine but not cationic lipids promotes transgene delivery to the nucleus in mammalian cells. J Biol Chem. Mar. 27, 1998;273(13):7507-11.
Rejman et al., Role of clathrin- and caveolae-mediated endocytosis in gene transfer mediated by lipo- and polyplexes. Mol Ther. Sep. 2005;12(3):468-74.
Rejman et al., Size-dependent internalization of particles via the pathways of clathrin- and caveolae-mediated endocytosis. Biochem J. Jan. 1, 2004;377(Pt 1):159-69.
Rui et al., Carboxylated branched poly(β-amino ester) nanoparticles enable robust cytosolic protein delivery and CRISPR-Cas9 gene editing. Sci Adv. Dec. 6, 2019;5(12):eaay3255. 11 pages.
Santos et al., Continuous Production of Discrete Plasmid DNA-Polycation Nanoparticles Using Flash Nanocomplexation. Small. Dec. 2016;12(45):6214-6222.
Thurston et al., Galectin 8 targets damaged vesicles for autophagy to defend cells against bacterial invasion. Nature. Jan. 15, 2012;482(7385):414-8.
Tockary et al., Single-Stranded DNA-Packaged Polyplex Micelle as Adeno-Associated-Virus-Inspired Compact Vector to Systemically Target Stroma-Rich Pancreatic Cancer. ACS Nano. Nov. 26, 2019;13(11):12732-12742.
Van Der Loo et al., Progress and challenges in viral vector manufacturing. Hum Mol Genet. Apr. 15, 2016;25(R1):R42-52.
Wang et al., Adeno-associated virus vector as a platform for gene therapy delivery. Nat Rev Drug Discov. May 2019;18(5):358-378.
Williford et al., Critical Length of PEG Grafts on lPEI/DNA Nanoparticles for Efficient in Vivo Delivery. ACS Biomater Sci Eng. Apr. 11, 2016;2(4):567-578.
Wilson et al., A Triple-Fluorophore-Labeled Nucleic Acid pH Nanosensor to Investigate Non-viral Gene Delivery. Mol Ther. Jul. 5, 2017;25(7):1697-1709.
Yue et al., Revisit complexation between DNA and polyethylenimine—Effect of uncomplexed chains free in the solution mixture on gene transfection. J Control Release. Oct. 10, 2011;155(1):67-76.
Zhang et al., Nano-Structural Effects on Gene Transfection: Large, Botryoid-Shaped Nanoparticles Enhance DNA Delivery via Macropinocytosis and Effective Dissociation. Theranostics. Feb. 2, 2019;9(6):1580-1598.8
Perevyazko I.Y., et al., "Polyelectrolyte Complexes of DNA and Linear PEI: Formation, Composition and Properties", Langmuir, Nov. 5, 2012, vol. 28, No. 46, pp. 16167-16176 (11 Pages), DOI: 10.1021/la303094b.
Wang X., et al., "Quantitation of Complexed Versus Free Polymers in Interpolyelectrolyte Polyplex Formulations", ACS Macro Letters, Nov. 8, 2013, vol. 2, No. 11, pp. 1038-1041 (5 Pages), DOI: 10.1021/mz400500q.
He Z., et al., "Scalable Production of Core-shell Nanoparticles by Flash Nanocomplexation to Enhance Mucosal Transport for Oral Delivery of Insulin", Nanoscale, vol. 10, No. 7, Jan. 25, 2017, pp. 3307-3319, XP055847190, United Kingdom, ISSN: 2040-3364, DOI: 10.1039/C7NR08047F, p. 3308, scheme 1, p. 3309, first column, p. 3312.
He Z., et al., "Size-Controlled Lipid Nanoparticle Production Using Turbulent Mixing to Enhance Oral DNA Delivery," Acta Biomaterialia, Sep. 27, 2018, vol. 81, pp. 195-207, XP085528666, ISSN: 1742-7061, DOI: 10.1016/J.ACTBIO.2018.09.047, figure 2.
Sang Y., et al., "Salt Ions and Related Parameters Affect PEI-DNA Particle Size and Transfection Efficiency in Chinese Hamster Ovary Cells", Cytotechnology, Springer Netherlands, Dordrecht, vol. 67, No. 1, Oct. 29, 2013, pp. 67-74, XP035427601, ISSN: 0920-9069, DOI: 10.1007/S10616-013-9658-Z, p. 69, second column.
Supplementary European Search Report for European Application No. 22756830.0, mailed May 20, 2025, 13 Pages.
Tripathi S.K., et al., "Surface Modification of Crosslinked Dextran Nanoparticles Influences Transfection Efficiency of Dextran-polyethylenimine Nanocomposites", Soft Matter, vol. 7, No. 24, Jan. 1, 2011, pp. 11360-11371, XP055783097, GB, ISSN: 1744-683X, DOI: 10.1039/c1sm06227a, abstract.

COMPOSITION OF SHELF-STABLE PLASMID DNA/POLYETHYLENEIMINE (PEI) PARTICLES WITH DEFINED SIZES FOR VIRAL VECTOR PRODUCTION AND METHOD FOR PREPARATION OF THE SAME

RELATED APPLICATION INFORMATION

This application is a national stage application under 35 U.S.C. § 371 of PCT/US2022/016584, filed Feb. 16, 2022, which claims priority to U.S. Application No. 63/149,983 filed on Feb. 16, 2021, the contents of which are herein incorporated by reference.

STATEMENT OF GOVERNMENTAL INTEREST

This invention was made with government support under grant EB018358 awarded by the National Institutes of Health. The government has certain rights in the invention.

BACKGROUND

Gene therapy has become increasingly available in treating various genetic and acquired diseases. Most of these therapies are delivered using viral vectors, such as vectors derived from lentivirus, retroviruses, and adeno-associated virus (AAVs). One of the most common methods to produce these vectors is transient transfection of a HEK293 packaging cell line or derivative thereof with plasmid DNAs (pDNAs) encoding viral accessory proteins and a transfer plasmid that contains the vector backbone. Benchmark transfection reagents include calcium phosphate, lipofectamine, and poly(ethyleneimine) (PEI). In a typical transfection procedure using PEI, for example, pDNA and PEI are separately dissolved in a serum-reduced medium and then mixed to form pDNA/PEI nanoparticles through charge-mediated complex coacervation. Following a predetermined incubation period, the complex particles are added into cell cultures. The complex coacervation with PEI facilitates cell entry, endosomal escape, and nuclear transport of pDNAs, resulting in expression of the viral accessory proteins.

Demands for the production of viral vectors have increased. To meet these increased demands, scalable, and reproducible production methods are essential to ensure consistent delivery of safe and efficacious therapeutic outcomes. The widely adopted method to manually prepare pDNA/PEI particles immediately before transfection suffers, however, from high batch-to-batch variations. Accordingly, the field can benefit from a solution to reduce the experimental variability and achieve maximum transfection efficiency using an off-the-shelf pDNA/PEI particle product with ease-of-use features and a sufficiently high DNA concentration to reduce dosage volumes.

SUMMARY

Accordingly, in some aspects, the presently disclosed subject matter provides a method for preparing a plurality of polycationic/nucleic acid nanoparticles, the method comprising:

(a) flowing a first stream comprising one or more water-soluble polycationic polymers at a first variable flow rate and a second stream comprising one or more nucleic acids at a second variable flow rate into a first flash nanocomplexation (FNC) mixer to form a plurality of nanoparticles having a first particle size;

(b) flowing a third stream comprising the plurality of nanoparticles having a first particle size at a third variable flow rate and a fourth stream comprising an assembly buffer at a fourth variable flow rate into a second FNC mixer to form a plurality of assembled nanoparticles;

(c) incubating the plurality of assembled nanoparticles formed in step (b) for a period of time to form a plurality of assembled nanoparticles having a second particle size; and (d) flowing a fifth stream comprising the plurality of assembled nanoparticles having a second particle size at a fifth variable flow rate and a sixth stream comprising a stabilization buffer at a sixth variable flow rate into a third FNC mixer to form a plurality of polycationic/nucleic acid nanoparticles.

In some aspects, the one or more water-soluble polycationic polymers are selected from the group consisting of polyethylenimine (PEI), chitosan, PAMAM dendrimers, protamine, poly(arginine), poly(lysine), poly(beta-aminoesters), cationic peptides and derivatives thereof. In particular aspects, the one or more water-soluble polycationic polymers is polyethylenimine.

In some aspects, the first stream comprising one or more water-soluble polycationic polymers have a concentration of polyethylenimine ranging from about 0.04 mg/mL to 3 mg/mL.

In certain aspects, the one or more nucleic acids are selected from the group consisting of an antisense oligonucleotide, cDNA, genomic DNA, guide RNA, plasmid DNA, vector DNA, mRNA, miRNA, piRNA, shRNA, and siRNA. In particular aspects, the one or more nucleic acids comprise plasmid DNA or a mixture of different species of plasmid DNA.

In particular aspects, the one or more nucleic acids comprise a mixture of one or more plasmid DNAs, wherein the one or more plasmid DNAs comprise a transfer plasmid and plasmid DNAs encoding a gag protein, a pol protein, a rev protein, and an env protein.

In some aspects, the transfer plasmid encodes a lentiviral vector.

In certain aspects, the lentiviral vector comprises a modified left (5') lentiviral LTR comprising a heterologous promoter, a Psi packaging sequence (Ψ+), a cPPT/FLAP, an RRE, a promoter operably linked to a polynucleotide encoding a therapeutic transgene, and a modified SIN (3') lentiviral LTR.

In other aspects, the env protein comprises a VSV-g envelope glycoprotein.

In some aspects, the second stream comprising one or more nucleic acids have a DNA concentration ranging from about 20 μg/mL to 800 μg/mL.

In some aspects, the first variable flow rate, the second variable flow rate, the third variable flow rate, the fourth variable flow rate, the fifth variable flow rate, and the sixth variable flow rate are each independently between about 5 mL/min to about 400 mL/min.

In some aspects, the first particle size has a range between about 40 nm to about 120 nm. In certain aspects, the plurality of nanoparticles having a first particle size are formed under conditions at a pH of about 2.0 to 4.0, and a conductivity of about 0.05 to 2.0 mS $cm^{-1}$.

In some aspects, the assembly buffer in step (b) comprises phosphate buffered saline. In certain aspects, the assembly buffer has a conductivity of about 2.0 to 25.0 mS $cm^{-1}$. In certain aspects, the assembly buffer has a pH from about 6.0 to about 8.0. In certain aspects, the phosphate buffered saline comprises one or more of NaCl, KCl, $Na_2HPO_4$, $KH_2PO_4$, and combinations thereof.

In some aspects, the plurality of nanoparticles formed in step (b) are incubated at about room temperature (22±4° C.) for a period of time.

In some aspects, the period of time ranges from about 0.2 to about 5 hours.

In some aspects, the second particle size has a range between about 300 nm to about 500 nm.

In some aspects, the plurality of polycationic/nucleic acid nanoparticles of step (d) are formed under conditions at a pH of about 2.0 to 4.0, and a conductivity of about 1.0 to 15.0 mS $cm^{-1}$.

In some aspects, the stabilization buffer comprises at least one sugar. In certain aspects, the sugar comprises trehalose. In particular aspects, the one or more sugars comprise between about 10% to about 30% w/w of trehalose. In particular aspects, the stabilization buffer comprises HCl. In yet more particular aspects, the stabilization buffer comprises between about 0.25 mmol/L to 20 mmol/L of protons.

In some aspects, the presently disclosed method further comprises lyophilizing or freezing the particles at about −80° C. for storage.

In other aspects, the presently disclosed subject matter provides a plurality of polycationic/nucleic acid nanoparticles comprising about 67±5 w/w % DNA; 9±5 w/w % bound polyethylenimine (PEI); and 24±5 w/w % residual polyethylenimine (PEI). In some aspects, the plurality of polycationic/nucleic acid nanoparticles has an average zeta potential is about 35±5 mV. In some aspects, the plurality of polycationic/nucleic acid nanoparticles has a particle size ranging from about 300 nm to about 500 nm. In some aspects, the particle size is selected from the group consisting of 300 nm, 400 nm, and 500 nm. In some aspects, the plurality of polycationic/nucleic acid nanoparticles has a polydispersity index of about 0.15±0.05 for a z-average particle size of 300 nm, a polydispersity index of about 0.25±0.05 for a z-average particle size of 400-nm, and a polydispersity index of about 0.35±0.05 for a z-average particle size of 500-nm.

In other aspects, the presently disclosed subject matter provides a method for preparing a viral vector, the method comprising contacting one or more cells with a polycationic/nucleic acid nanoparticle prepared by the presently disclosed methods or the plurality of polycationic/nucleic acid nanoparticles described herein. In certain aspects, the one or more cells comprise HEK293 cells. In particular aspects, the one or more cells comprise HEK293S cells, HEK293T cells, HEK293F cells, HEK293FT cells, HEK293FTM cells, HEK293SG cells, HEK293SGGD cells, HEK293H cells, HEK293E cells, HEK293MSR cells, or HEK293A cells. In particular aspects, the one or more cells comprise HEK293T cells. In more particular aspects, the one or more cells comprise HEK293T cells adapted for suspension culture.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
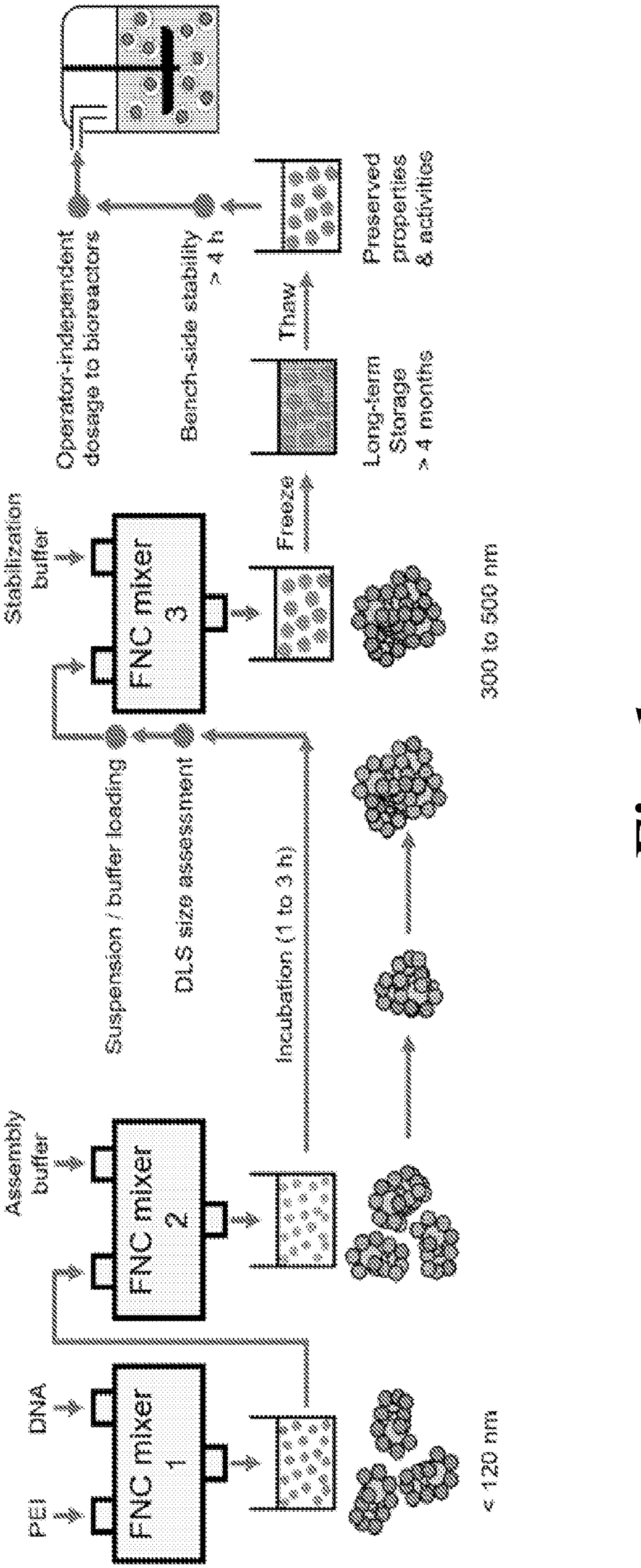
Figure 2:
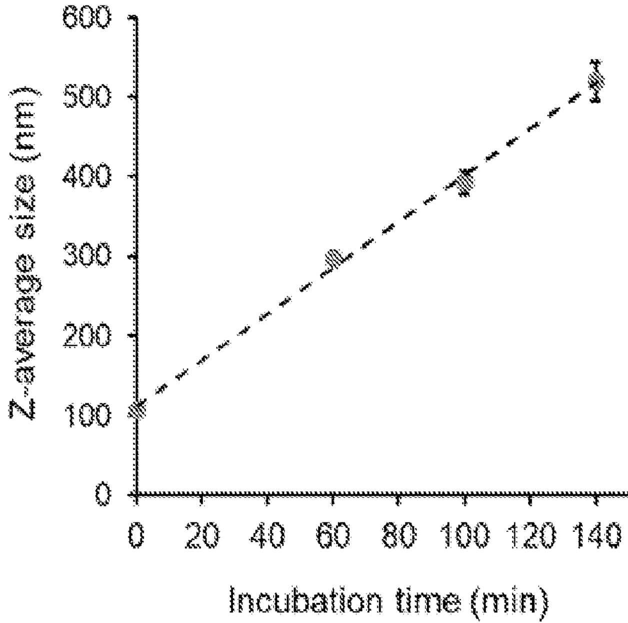

Having thus described the presently disclosed subject matter in general terms, reference will now be made to the accompanying Figures, which are not necessarily drawn to scale, and wherein:

FIG. 1 is schematic showing a procedural overview for producing DNA/polyethylenimine (PEI) particles having a particle size between 300 nm to 500 nm. Preferred pDNA/PEI particles for producing lentivirus vector (LVV) have a z-average size (the Z average is the intensity weighted mean hydrodynamic size of the ensemble collection of particles measured by dynamic light scattering (DLS)) of between about 400 nm to about 500 nm;

FIG. 2 shows the growth kinetics of particles during incubation upon mixing with the assembly buffer. In this example, an initial DNA concentration of 200 μg/mL, a PEIpro® concentration of 0.53 mg/mL, an assembly buffer with 54.8 mmol/L NaCl, 1.08 mmol/L KCl, 4 mmol/L $Na_2HPO_4$ and 0.72 mmol/L $KH_2PO_4$ are used. Under this condition, the growth is reproducible and can be modeled as:

$$\text{Size [nm]} = 2.9 \times \text{Time } [h] + 111.6;$$

Figures 3A, 3B, 3C:
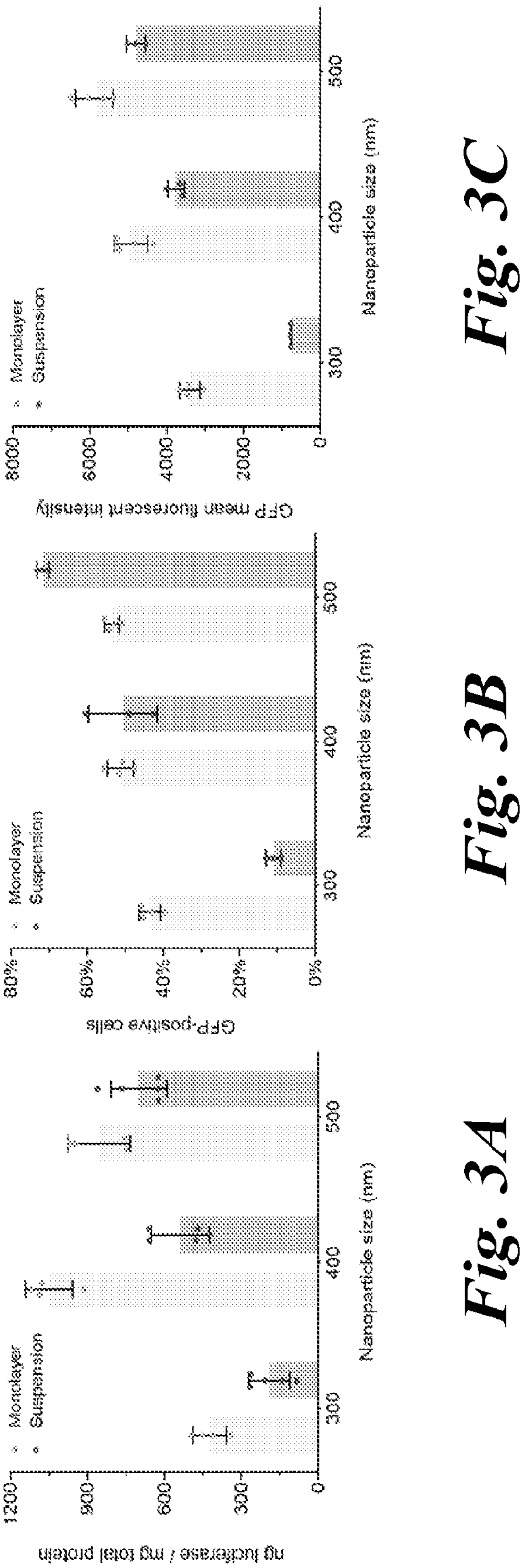
Figures 4A, 4B, 4C, 4D:
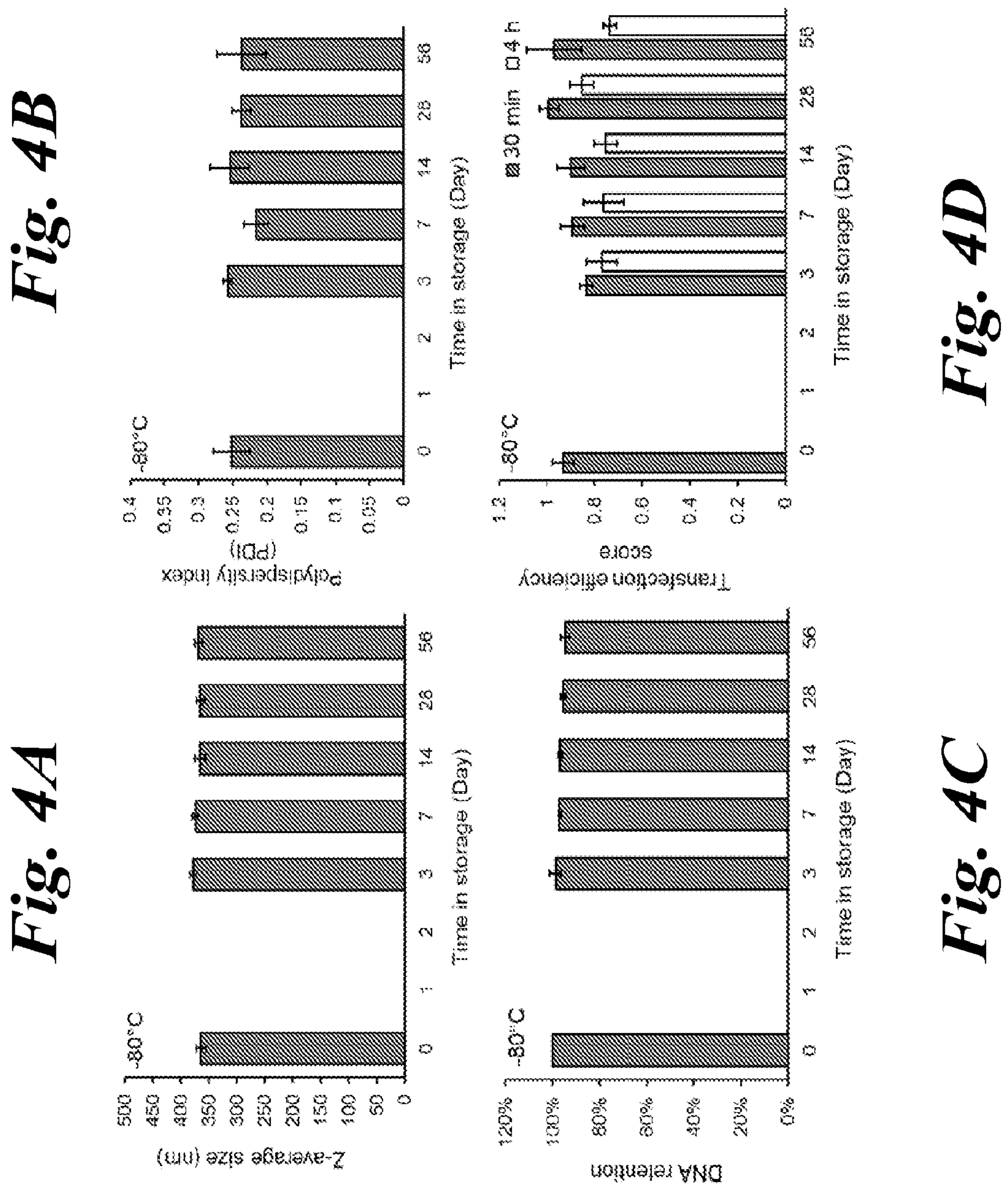

FIG. 3A, FIG. 3B, and FIG. 3C show the transfection efficiencies of stable particles with a controlled size ranging from about 60 nm to about 1000 nm. FIG. 3A shows the efficiency of transgene expression of luciferase as a reporter. FIG. 3B and FIG. 3C show the efficiency of transgene expression of GFP for percentage of GFP-positive cells (FIG. 3B) and for the mean fluorescent intensity in the population of GFP-positive cells (FIG. 3C);

FIG. 4A, FIG. 4B, FIG. 4C, and FIG. 4D show the long-term stability of 400-nm particles stored at a temperature under −80° C. after a standard production process. FIG. 4A shows the z-average size measured by DLS. FIG. 4B shows the polydispersity index (PDI) measured by DLS. FIG. 4C shows the DNA retention measured by NanoDrop DNA concentration assessment. FIG. 4D shows the transfection efficiency of thawed particles, for which a 30-minute or 4-h period was applied after the thawed particle suspension had reached room temperature. A transfection efficiency score of 1 means equivalent transfection efficiency compared to the highest that could be achieved by manual preparation method of the particles; and FIG. 5A, FIG. 5B, FIG. 5C, and FIG. 5D demonstrate the effect of pDNA/PEI particle size on the infectious titers (FIG. 5A) and P:I ratios (FIG. 5B) of the LVVs produced in the 15-mL small bioreactors (Ambr 15). 1× dosage level represents 1 μg pDNA $mL^{-1}$ in the suspension cultures. The power of each size group differed in the experimental design and is fully indicated by the individual data points shown in the figures. FIG. 5C and FIG. 5D show the infectious titers (FIG. 5C) and P:I ratios (FIG. 5D) of LVVs produced in a 2-1 bioreactor using the 400-nm pDNA/PEI particles, at a dosage level of 1 μg pDNA $mL^{-1}$. n=1 bioreactor for each condition. In FIG. 5A to FIG. 5D, the control level represents the optimal results from the standardized in-house procedures to prepare pDNA/PEI particles manually immediately before the transfection experiments.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

No methods currently exist for generating concentrated, stable, off-the-shelf DNA/polyethylenimine (PEI) particles for reproducible transfection of cells, e.g., HEK293 cells or derivatives thereof, to produce viral vectors. The presently disclosed subject matter simplifies and streamlines the transfection process, thereby making it operator-independent and facilitates scale-up production of viral vectors. The presently disclosed subject matter also addresses the poor reproducibility and inconsistent yield in production of viral vectors via a transient transfection process. Accordingly, the presently disclosed subject matter will lead to off-the-shelf particle formulations that is, in some embodiments, between 400 nm to 500 nm in size for lentivirus vector (LVV) production.

In some embodiments, the presently disclosed subject matter provides a method for preparing shelf-stable DNA/PEI particles having defined sizes. Referring now to FIG. 1, the presently disclosed method can be separated into three distinct steps, including:

(1) generating plasmid DNA/PEI nanoparticles having a particle size less than about 120-nm as so-called "base units" for assembly. This first step is achieved using a flash nanocomplexation process to ensure higher uniformity in size and composition and size control between about 40 nm to about 120 nm. Other methods known in the art can be used to generate these base-unit nanoparticles;

(2) inducing nanoparticle assembly by controlling the ionic strength (increasing salt concentration) and reducing the surface charge density (increasing pH). This step is achieved by mixing the 40- to 120-nm base-unit nanoparticles with an assembly buffer inside an FNC mixing chamber under a flow condition and holding the solution at room temperature for a predetermined amount of time to yield the desired particle size range of about 300 nm to about 500 nm. Since the growth of the particle size can be modeled with controlled kinetics, the size of the particles is controlled by adjusting the pH and salt concentration of the assembly buffer and by tuning the time of incubation; and (3) arresting the growth and stabilizing the particles by reducing ionic strength and increasing the surface charge density (reducing pH). This step is achieved by mixing the particles in the assembly solution with the stabilization solution inside an FNC mixing chamber under a flow condition.

The resulting particles can be stored in suspension form at −80° C. The stabilization solution (media) can afford exceedingly high degree of stability on the shelf, thereby enabling this formulation to be an off-the-shelf product.

A. Method for Preparing Polycationic/Nucleic Acid Nanoparticles

Accordingly, in some embodiments, the presently disclosed subject matter provides a method for preparing a plurality of polycationic/nucleic acid nanoparticles, the method comprising:

(a) flowing a first stream comprising one or more water-soluble polycationic polymers at a first variable flow rate and a second stream comprising one or more nucleic acids at a second variable flow rate into a first flash nanocomplexation (FNC) mixer to form a plurality of nanoparticles having a first particle size;

(b) flowing a third stream comprising the plurality of nanoparticles having a first particle size at a third variable flow rate and a fourth stream comprising an assembly buffer at a fourth variable flow rate into a second FNC mixer to form a plurality of assembled nanoparticles;

(c) incubating the plurality of assembled nanoparticles formed in step (b) for a period of time to form a plurality of assembled nanoparticles having a second particle size; and (d) flowing a fifth stream comprising the plurality of assembled nanoparticles having a second particle size at a fifth variable flow rate and a sixth stream comprising a stabilization buffer at a sixth variable flow rate into a third FNC mixer to form a plurality of polycationic/nucleic acid nanoparticles.

In some embodiments, the one or more water-soluble polycationic polymers are selected from the group consisting of polyethylenimine (PEI), chitosan, PAMAM dendrimers, protamine, poly(arginine), poly(lysine), poly(beta-aminoesters), cationic peptides and derivatives thereof. In particular embodiments, the one or more water-soluble polycationic polymers is polyethylenimine.

In some embodiments, the first stream comprising one or more water-soluble polycationic polymers have a concentration of polyethylenimine ranging from about 0.04 mg/mL to 3 mg/mL.

In certain embodiments, the one or more nucleic acids are selected from the group consisting of an antisense oligonucleotide, cDNA, genomic DNA, guide RNA, plasmid DNA, vector DNA, mRNA, miRNA, piRNA, shRNA, and siRNA. In particular embodiments, the one or more nucleic acids comprise plasmid DNA or a mixture of different species of plasmid DNA.

In particular embodiments, a mixture of pDNAs encode a transfer plasmid comprising a packageable viral vector and one or more viral structural/accessory proteins necessary and sufficient to produce a viral vector.

In some embodiments, the second stream comprising one or more nucleic acids have a DNA concentration ranging from about 20 μg/mL to 800 μg/mL.

In some embodiments, the first variable flow rate, the second variable flow rate, the third variable flow rate, the fourth variable flow rate, the fifth variable flow rate, and the sixth variable flow rate are each independently between about 5 mL/min to about 400 mL/min.

In some embodiments, the first particle size has a range between about 40 nm to about 120 nm. In some embodiments, the plurality of nanoparticles having a first particle size are formed under conditions at a pH of about 2.0 to 4.0, and a conductivity of about 0.05 to 2.0 mS $cm^{-1}$.

In some embodiments, the assembly buffer in step (b) comprises phosphate buffered saline. In some embodiments, the assembly buffer has a conductivity of about 2.0 to 25.0 mS $cm^{-1}$. In certain embodiments, the assembly buffer has a pH from about 6.0 to about 8.0. In certain embodiments, the phosphate buffered saline comprises one or more of NaCl, KCl, $Na_2HPO_4$, $KH_2PO_4$, and combinations thereof.

In some embodiments, the plurality of nanoparticles formed in step (b) are incubated at about room temperature (22±4° C.) for a period of time.

In some embodiments, the period of time ranges from about 0.2 to about 5 hours.

In some embodiments, the second particle size has a range between about 300 nm to about 500 nm.

In some embodiments, the plurality of polycationic/nucleic acid nanoparticles of step (d) are formed under conditions at a pH of about 2.0 to 4.0, and a conductivity of about 1.0 to 15.0 mS $cm^{-1}$.

In some embodiments, the stabilization buffer in step (d) comprises at least one sugar. In certain embodiments, the sugar comprises trehalose. In particular embodiments, the one or more sugars comprise between about 10% to about 30% w/w of trehalose. In particular embodiments, the stabilization buffer comprises HCl. In yet more particular embodiments, the stabilization buffer comprises between about 0.25 mmol/L to 20 mmol/L of protons.

In some embodiments, the presently disclosed method further comprises lyophilizing or freezing the particles at about −80° C. for storage.

B. Characteristics of Polycation/Nucleic Acid Nanoparticles

In other embodiments, the presently disclosed subject matter provides a plurality of polycationic/nucleic acid nanoparticles comprising about 67±5 w/w % DNA; 9±5 w/w % bound polyethylenimine (PEI); and 24±5 w/w % residual polyethylenimine (PEI). In some embodiments, the plurality of polycationic/nucleic acid nanoparticles has an average zeta potential is about 35±5 mV. In some embodiments, the plurality of polycationic/nucleic acid nanoparticles has a particle size ranging from about 300 nm to about 500 nm. In some embodiments, the particle size is selected from the group consisting of 300 nm, 400 nm, and 500 nm. In some embodiments, the plurality of polycationic/nucleic acid nanoparticles has a polydispersity index of about 0.15±0.05 for a z-average particle size of 300 nm, a polydispersity index of about 0.25±0.05 for a z-average particle size of 400-nm, and a polydispersity index of about 0.35±0.05 for a z-average particle size of 500-nm.

C. Method for Preparing a Viral Vector

In other embodiments, the presently disclosed subject matter provides a method for preparing a viral vector, the method comprising contacting one or more cells with a polycationic/nucleic acid nanoparticle prepared by the presently disclosed methods or the plurality of polycationic/nucleic acid nanoparticles described herein.

In particular embodiments, one or more cells are transfected with a polycationic/nucleic acid nanoparticle, e.g., a pDNA/PEI complex, contemplated herein to generate viral vector.

Illustrative examples of cells suitable for transfection with the nanoparticles contemplated herein include, but are not limited to CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRCS cells, A549 cells, HT1080 cells, 293 cells, B-50 cells, 3T3 cells, NIH3T3 cells, HepG2 cells, Saos-2 cells, Huh7 cells, HeLa cells, W163 cells, 211 cells, 211A cells, or derivatives thereof.

In preferred embodiments, cells suitable for transfection with the nanoparticles contemplated herein comprise HEK293 cells or a derivative thereof. Derivatives of HEK293 cells suitable for use in particular embodiments contemplated herein include, without limitation, HEK293S cells, HEK293T cells, HEK293F cells, HEK293FT cells, HEK293FTM cells, HEK293SG cells, HEK293SGGD cells, HEK293H cells, HEK293E cells, HEK293MSR cells, and HEK293A cells.

In other particular preferred embodiments, the one or more cells comprise HEK293T cells adapted to suspension culture.

In some embodiments, the viral vector is a retroviral vector. Illustrative examples of retroviral vectors suitable for use in particular embodiments contemplated herein include but are not limited to vectors derived from Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

In preferred embodiments, the viral vector is a lentiviral vector. Illustrative examples of lentiviral vectors suitable for use in particular embodiments contemplated herein include but are not limited to vectors derived from HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In more preferred embodiments, lentiviral vectors are derived from HIV-1 or HIV-2.

In particular embodiment, a transfer plasmid encodes a lentiviral vector that comprises a left (5') lentiviral LTR, a Psi packaging sequence (Ψ+), a central polypurine tract/DNA flap (cPPT/FLAP), a rev response element (RRE), a promoter operably linked to a polynucleotide encoding a therapeutic transgene, and a right (3') lentiviral LTR. Lentiviral vectors may optionally comprise post-transcriptional regulatory elements including, but not limited to, polyadenylation sequences, insulators, a woodchuck hepatitis virus posttranscriptional regulatory element (WPRE), a hepatitis B virus (HPRE), and the like.

In particular embodiment, a transfer plasmid a lentiviral vector that comprises a modified left (5') lentiviral LTR comprising a heterologous promoter, a Psi packaging sequence (Ψ+), a central polypurine tract/DNA flap (cPPT/FLAP), a rev response element (RRE), a promoter operably linked to a polynucleotide encoding a therapeutic transgene, and a modified (3') lentiviral LTR.

In particular embodiments, a transfer plasmid a lentiviral vector that comprises a modified 5' LTR wherein the U3 region of the 5' LTR is replaced with a heterologous promoter to drive transcription of the viral genome during production of viral particles.

Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

In particular embodiments, a transfer plasmid a lentiviral vector that comprises a modified self-inactivating (SIN) 3' LTR that renders the viral vector replication defective. SIN vectors comprise one or more modifications of the U3 region in the 3' LTR to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In particular embodiments, the 3' LTR is modified such that the U3 region is deleted and the R and/or U5 region is replaced, for example, with a heterologous or synthetic poly(A) sequence, one or more insulator elements, and/or an inducible promoter.

In particular embodiments, one or more pDNAs encode a transfer plasmid comprising a packageable viral vector genome and one or more of the viral structural/accessory proteins selected from the group consisting of: gag, pol, env, tat, rev, vif, vpr, vpu, vpx, and nef. In preferred embodiments, the viral structural/accessory proteins are selected from the group consisting of: gag, pol, env, tat, and rev. In more preferred embodiments, the viral structural/accessory proteins are selected from the group consisting of: gag, pol, env, and rev or gag, pol, and env.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120.

Illustrative examples of env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other embodiments, env proteins suitable for use in particular embodiments include, but are not limited to any of the following viruses: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In preferred embodiments, the env gene encodes a VSV-G envelope glycoprotein.

In some preferred embodiments, pDNA/PEI complexes contemplated herein comprise a transfer plasmid encoding a lentiviral vector comprising a modified left (5') lentiviral LTR comprising a heterologous promoter, a Psi packaging sequence (Ψ+), a cPPT/FLAP, an RRE, a promoter operably linked to a polynucleotide encoding a therapeutic transgene, and a modified SIN (3') lentiviral LTR; a plasmid encoding a lentiviral gag/pol, a plasmid encoding rev, and a plasmid encoding an env gene, preferably a VSV-G envelope glycoprotein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject. In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Preparation of Base-Unit DNA/PEI Nanoparticles

A lentiviral vector transfer plasmid and plasmids encoding lentiviral gag/pol, rev, and VSV-g were diluted to a total final DNA concentration of 20 μg/mL to 800 μg/mL and combined. There is no limitation on the number of species of, the length of, or the specific gene map of the plasmids.

The plasmid solution and the diluted PEIpro® solution (0.04 mg/mL to 3 mg/mL) are loaded onto two separate NORM-JECT syringes and connected to a confined impinging jet (CIJ) device. The solutions are infused into the CIJ device controlled by a digital syringe pump under a flow rate of 10 mL/min to 40 mL/min. The resultant eluant suspension of nanoparticles has a Z-average size of 40 nm to 120 nm.

Example 2

PEC Nanoparticle Assembly and Growth Control

The assembly buffer is prepared to have different ionic strengths from 34.3 mM to 343 mM at a pH between about 7.0 to about 7.4. Phosphate buffered saline (PBS) typically was used to prepare the assembly buffer. The corresponding concentrations of each components are: 0.2×PBS (27.4 mmol/L NaCl, 0.54 mmol/L KCl, 2 mmol/L $Na_2HPO_4$, and 0.36 mmol/L $KH_2PO_4$; with an ionic strength of 32.5 mM) to 2×PBS (274 mmol/L NaCl, 5.4 mmol/L KCl, 20 mmol/L $Na_2HPO_4$, and 3.6 mmol/L $KH_2PO_4$; with an ionic strength of 325.4 mM), All components are typically varied proportionally.

The base-unit nanoparticle suspension prepared from Example 1 and the assembly buffer are loaded into two separate syringes and connected to a CIJ device. The solutions are injected into the CIJ device controlled by a digital syringe pump at a flow rate of 10 mL/min to 40 mL/min. The collected suspension of particles is incubated at room temperature (22±4° C.) for predetermined times to grow to the desired size of 300 nm to 500 nm. For example, when an initial DNA concentration of 200 μg/mL, a PEIpro® concentration of 0.53 mg/mL, an assembly buffer with an ionic strength of 68.6 mM (54.8 mmol/L NaCl, 1.08 mmol/L KCl, 4 mmol/L $Na_2HPO_4$ and 0.72 mmol/L $KH_2PO_4$) are used, the incubation times are 60 minutes for the 300-nm particles, 100 minutes for the 400-nm particles, and 140 minutes for the 500-nm particles, respectively (FIG. 2).

Example 3

PEC Nanoparticle Stabilization and Lyophilization

The stabilization buffer with 0.25 mmol/L to 20 mmol/L of protons (for example HCl solution) and 19% w/w trehalose and the assembled particle suspension obtained in Example 2 are loaded into two separate syringes which are connected to a CIJ device. The solutions are infused into the CIJ device controlled by a digital syringe pump at a flow rate of 10 mL/min to 40 mL/min. The stabilized particles can be lyophilized or frozen down to −80° C. for storage.

Example 4

Compositions and Characterization of the Assembled Particles

The optimized DNA/PEI particles refer to a size-defined, shelf-stable suspension comprising plasmid DNA/PEI complexes prepared from a mixture of multiple species of plasmids and PEIpro® at a total concentration of plasmids at 50 μg DNA per mL. The particles have the z-average size of 300 nm to 500 nm according to the dynamic light scattering (DLS) measurements. A representative quality control sheet is shown below in Table 1. The particles can be stored in a frozen suspension form for more than 2 months at −80° C.

The compositions of the assembled particles are as follows regardless of the particle size: 67±5 w/w % DNA; 9±5 w/w % bound PEI; and 24±5 w/w % residual PEI. The average zeta potential for all particles was 35±5 mV. The typical polydispersity index is 0.15±0.05 for a z-average size of 300 nm; 0.25±0.05 for 400-nm particles, and 0.35±0.05 for 500-nm particles.

A representative quality control sheet for three example batches of the assembled particles at 300 nm, 400 nm, or 500 nm are listed in Table 1.

TABLE 1

Example of DLS and NanoDrop assessments of the particle quality upon production and a freezing-thawing cycle

| Batch | 20200917-300 | 20200917-400 | 20200917-500 |
|---|---|---|---|
| Target size | 300 nm | 400 nm | 500 nm |
| Target DNA concentration | 50 μg/mL | 50 μg/mL | 50 μg/mL |
| Freshly prepared samples | | | |
| Z-average diameter (DLS) | 297.6 ± 7.6 nm | 393.1 ± 14.5 nm | 519.7 ± 24.2 nm |
| PDI (DLS) | 0.176 ± 0.029 | 0.231 ± 0.046 | 0.378 ± 0.024 |
| DNA in suspension (NanoDrop) | 51.6 ± 0.5 μg/mL | 47.5 ± 0.8 μg/mL | 44.3 ± 2.0 μg/mL |
| 30 min after thawing from storage at −80° C. | | | |
| Z-average diameter (DLS) | 296.8 ± 5.2 nm | 404.1 ± 8.2 nm | 506.1 ± 20.1 nm |
| PDI (DLS) | 0.135 ± 0.024 | 0.237 ± 0.003 | 0.340 ± 0.103 |
| DNA in suspension (NanoDrop) | 51.7 ± 0.1 μg/mL | 47.8 ± 0.5 μg/mL | 42.8 ± 1.2 μg/mL |
| 6 h after thawing from storage at −80° C. | | | |
| Z-average diameter (DLS) | 294.7 ± 5.3 nm | 409.2 ± 12.0 nm | 509.5 ± 50.0 nm |
| PDI (DLS) | 0.181 ± 0.036 | 0.265 ± 0.023 | 0.394 ± 0.021 |
| DNA in suspension (NanoDrop) | 51.5 ± 0.8 μg/mL | 47.3 ± 0.6 μg/mL | 43.0 ± 1.5 μg/mL |

Example 5

Characterization of the Transfection Activity

In assessing the transfection efficiency of the stable particles produced using this method, a monolayer culture of HEK293T cell line at 20000 cells/well, and a suspension culture of HEK293F cell line at $0.5\times10^6$ cells/mL were seeded one day prior to dosage. For the monolayer culture, the particles are premixed with medium to a final DNA concentration of 1 μg/mL, then this particle-containing medium replaces the original culture medium. Medium refreshment and cell harvest happen at 4 h and 24 h post-dosage, respectively. For the suspension culture, the particles are directly injected to the cultured volume, followed by normal stirring required for suspension cells. Medium is never refreshed, and cells are harvest 48 h post-dosage. The typical results obtained under these conditions.

Example 6

Particle Reconstitution and Characterization of Shelf-Stability of DNA/PEI Particles by Transfection Efficiency in HEK293F Cell Suspension Culture A frozen stock of the particles is retrieved from −80° C. at different storage time points; and thawed by resting the samples at room temperature without any additional source of heating. When the sample reaches the room temperature, the particle suspension is briefly vortexed and then ready for use. The particle suspension is added to a suspension culture of HEK293F cells via pipetting or a pump depending on the culture size. The reconstituted particles preserved all the pre-freezing characteristics, including the average size, polydispersity index, and the DNA concentration (FIG. 4). Such stability was verified for at least 2 months. The thawed particle suspension is stable at room temperature for at least 4 h before use. This feature ensures operator-independent, robust, and reproducible transfection outcome and viral production quality and yield. The transfection efficiency of 400-nm particles is equivalent to the highest transfection efficiency achievable by particles manually produced used a standard operating procedure currently adopted by the industry and recommended by the reagent manufacturer (Polyplus Transfection®, 850 bd Sebastien Brant, 67400 Illkirch FRANCE).

Example 7

Production of LVVs on Ambr 15 Micro-Bioreactor

Particles at different sizes were produced, stored at −80° C. until use. Particles can be shipped overnight on dry ice; and upon arrival, the particles were stored under −80° C. until use. In-house suspension adapted HEK293T cells were seeded into 15 ml Ambr 15 micro-bioreactors (Sartorius Stedim Biotech, France). When cells reached a predetermined density, the cultures were perfused one vessel volume, then transfected with particles at an equivalent DNA concentration of 1 or 2 μg $mL^{-1}$ by addition of corresponding volumes of the thawed particles at 50 μg pDNA $mL^{-1}$ using the automated pipetting of the liquid handler. Parallel manually mixed pDNA/PEI particle transfections were performed using the same process conditions. After a predetermined incubation time, the micro-bioreactors were perfused one vessel volume again. The microbioreactor cultures were harvested and clarified by centrifugation at 500 g for 5 min. The supernatants were sampled for analysis. Infectious titer results in titer units per ml (TU $mL^{-1}$) were determined by qPCR and the capsid protein p24 (ng $mL^{-1}$) was assessed by an enzyme-linked immunosorbent assay (Alliance HIV-I p24 ELISA Plate Kit, Perkin Elmer, USA). The p24 value was an indicator of total LVV particles, and the ratio between infectious titer and p24 detected was derived to particle-to-infectivity (P:I) ratio. For example, a P:I of 100 means that there is one functional LVV out of 100 viral particles produced.

Figure 5A:
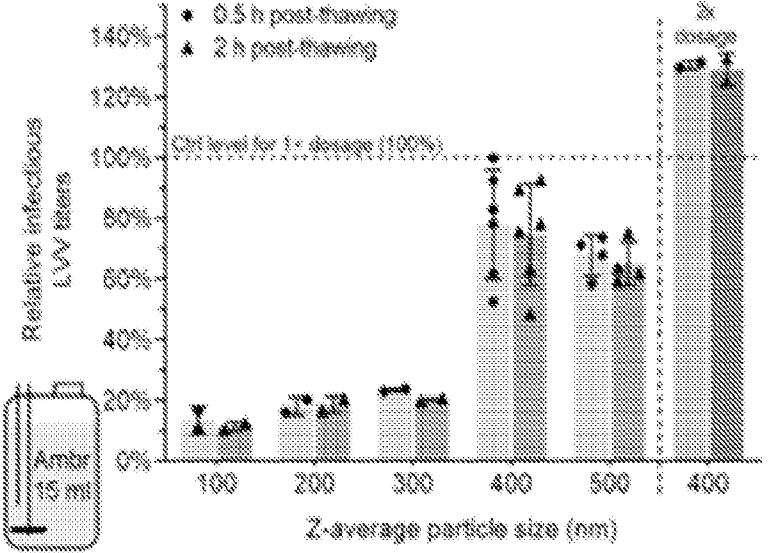
Figure 5B:
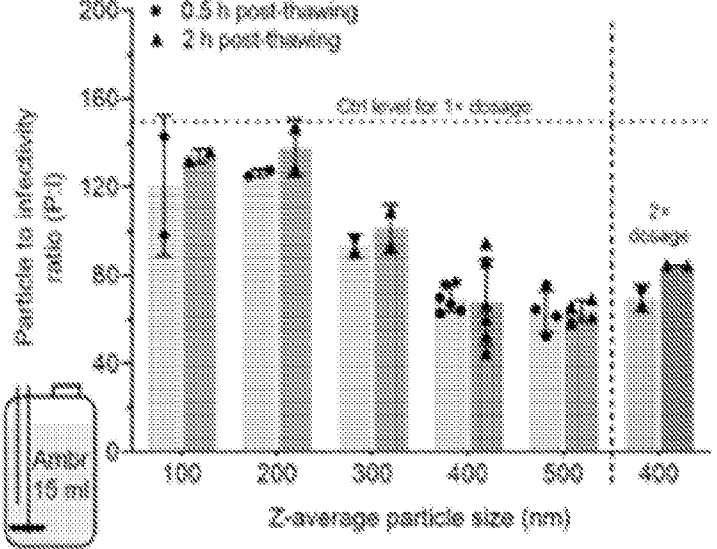
Figure 5C:
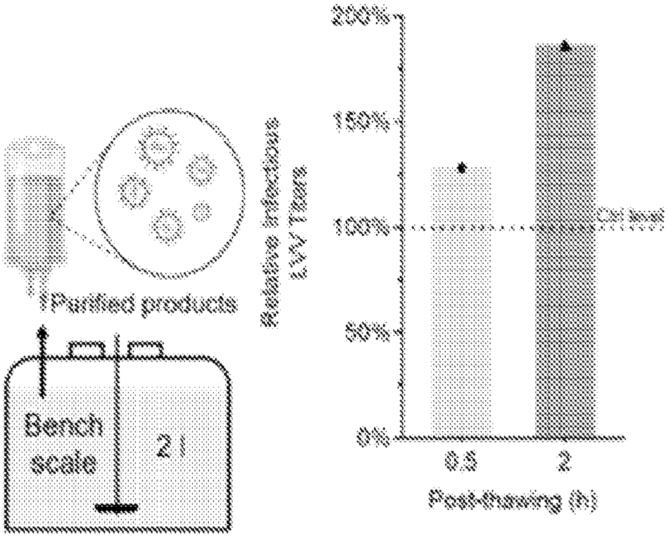
Figure 5D:
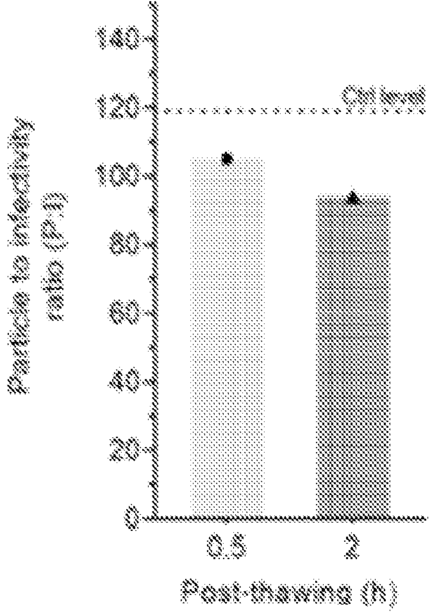

In these miniature-scale evaluations, LVV titers obtained from the culture supernatants increased with particle size from 100 to 400 nm, and then slightly decreased with 500-nm particles, which was consistent with the reporter gene transfection results (FIG. 5A). The 400-nm particles produced comparable titers (78%) as an internal control that represents the highest level of productivity achieved by perishable particles from the standard method. After 2-h standing on the bench at ambient temperature following thawing, the 400-nm particles delivered the same levels of transfection and LVV titers (FIG. 5A), demonstrating excellent stability of the particles that is difficult to achieve using the standard method. Further, the 400-nm particles demonstrated a dose-dependent response that was not seen in the standard method. The comparable titers by the 400-nm particles were achieved through production of fewer total number of LVVs by a higher proportion that was infectious than the control. This was indicated by a lowered particle-to-infectivity (P:I) ratio (FIG. 5B).

TABLE 1

Quality control parameters of particles prepared for bioreactor testing at Bluebird Bio Inc. for LVV production (Ambr 15 micro-bioreactor scale)

| Batch | A-100 | A-200 | A-300 | A-400 | A-500 |
|---|---|---|---|---|---|
| Target size (nm) | 100 | 200 | 300 | 400 | 500 |
| Target DNA concentration (μg mL$^{-1}$) | 50 | 50 | 50 | 50 | 50 |
| Production volumes (mL) | 10 | 10 | 10 | 20 | 10 |
| Freshly prepared samples | | | | | |
| Z-average diameter (nm) | 107.6 ± 0.5 | 195.2 ± 1.9 | 297.6 ± 7.6 | 393.1 ± 14.5 | 519.7 ± 24.2 |
| DNA in suspension (μg mL$^{-1}$) | 53.2 ± 0.4 | 49.1 ± 0.1 | 51.6 ± 0.5 | 47.5 ± 0.8 | 44.3 ± 2.0 |
| Freezing to −80° C., thawing to room temperature, immediately followed by measurements | | | | | |
| Z-average diameter (nm) | 107.3 ± 1.9 | 200.7 ± 4.6 | 296.8 ± 5.2 | 404.1 ± 8.2 | 506.1 ± 20.1 |
| DNA in suspension (μg mL$^{-1}$) | 52.8 ± 0.2 | 52.9 ± 0.4 | 51.7 ± 0.1 | 47.8 ± 0.5 | 42.8 ± 1.2 |
| Freezing to −80° C., thawing to room temperature, keeping on bench for 3 h before measurements | | | | | |
| Z-average diameter (nm) | 111.4 ± 1.5 | 196.2 ± 1.6 | 294.7 ± 5.3 | 409.2 ± 12.0 | 509.5 ± 50.0 |
| DNA in suspension (μg mL$^{-1}$) | 52.8 ± 0.3 | 51.1 ± 0.5 | 51.5 ± 0.8 | 47.3 ± 0.6 | 43.0 ± 1.5 |

Example 8

Production of LVVs at the Bench-Scale

The same suspension adapted HEK293T cell line was used and seeded into an in-house developed 2-1 single-use bioreactor. When cells reached a predetermined density, the cultures were perfused with one vessel volume utilizing an alternating tangential flow device, then transfected with particles at an equivalent DNA concentration of 1 or 1.5 mg mL$^{-1}$ by addition of corresponding volumes of the thawed particles at 50 mg pDNA mL$^{-1}$ using a peristaltic pump. The cultures were then harvested at the peak expression and clarified by depth filtration. Purification of the LVVs was then completed utilizing a standard resin-based chromatography followed by ultrafiltration and diafiltration into the final formulation. Infectious titer and p24 results were then determined using the described methods above.

Like the Ambr® 15 methods, thawed particle suspensions were added rapidly to the top of the cultures, with benchtop operations using a peristaltic pump. The vessels were batch harvested and purified prior to testing for titer. The infectious titers (with 0.5-h or 2-h stand after thawing) from these stabilized 400-nm particles were superior (128% and 187%, n=1 bioreactor for each) to the highest level by the standard preparation protocol (FIG. 5C), and a lower P:I ratio was also verified at this scale (FIG. 5D). These results suggest that the 400-nm particles might have improved co-expression of multiple plasmids essential for LVV production and assembly.

TABLE 2

Quality control parameters of particles prepared for bioreactor testing at Bluebird Bio Inc. for LVV production (bench-scale)

| Batch | B-400-01 | B-400-02 |
|---|---|---|
| Target size (nm) | 400 | 400 |
| Target DNA concentration (μg mL$^{-1}$) | 50 | 50 |
| Production volume (mL) | 100 | 70 |
| Experiments | Bench-scale | Bench-scale |

TABLE 2-continued

Quality control parameters of particles prepared for bioreactor testing at Bluebird Bio Inc. for LVV production (bench-scale)

| Batch | B-400-01 | B-400-02 |
|---|---|---|
| Freshly prepared samples | | |
| Z-average diameter (nm) | 393.3 ± 4.6 | 397.2 ± 3.2 |
| Polydispersity index (PDI) | 0.221 ± 0.018 | 0.238 ± 0.023 |
| DNA in suspension (μg $mL^{-1}$) | 48.1 ± 0.7 | 49.4 ± 1.4 |
| Freezing to −80° C., thawing to room temperature, immediately followed by measurements. | | |
| Z-average diameter (nm) | 414.9 ± 4.3 | 409.6 ± 0.6 |
| Polydispersity index (PDI) | 0.221 ± 0.047 | 0.231 ± 0.039 |
| DNA in suspension (μg $mL^{-1}$) | 49.8 ± 0.6 | 50.0 ± 1.8 |
| Freezing to −80° C., thawing to room temperature, keeping on bench for 3 h before measurements. | | |
| Z-average diameter (nm) | 405.8 ± 7.8 | 407.0 ± 18.7 |
| Polydispersity index (PDI) | 0.211 ± 0.021 | 0.247 ± 0.024 |
| DNA in suspension (μg $mL^{-1}$) | 48.8 ± 0.7 | 49.9 ± 0.5 |

Example 9

Example Summary

This study revealed the key insight that the transfection efficiency in LVV production cell lines was critically dependent on the size of pDNA/PEI particles and identified 400 nm to 500 nm as the optimal size range for transfection. A stepwise process was designed based on surface charge inversion and conditioning of ionic strength, and pDNA/PEI particles with an average size of 60 nm to 1000 nm were prepared with a high degree of size control. The prepared particles exhibited excellent stability in suspension at ambient temperature for standard operations and at −80° C. for long-term storage. This particle size engineering method confers high uniformity, and the sequential steps permits high tunability of the assembly kinetics. A scale-up production method was developed based on a continuous flow mixing process—the FNC platform—with a tailored assembly kinetics to accommodate the mixing procedure. The optimal transfection activity and stability of the 400-nm pDNA/PEI particle formulation was validated in production of LVVs using pre-prepared, freeze-stored, transported, and thawed particles, showing matching performance with the particles produced using the industry standard in realistic bioreactor settings. This new scalable manufacturing method has high translational potential that can be easily extended to production of a wide range of gene therapy vectors with improved productivity and quantity control.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Milone, M. C. and O'Doherty, U. Clinical use of lentiviral vectors. Leukemia 32, 1529-1541 (2018).

Wang, D., Tai, P. W. L. and Gao, G. Adeno-associated virus vector as a platform for gene therapy delivery. Nature Reviews Drug Discovery 18, 358-378 (2019).

Merten, O.-W., Hebben, M. and Bovolenta, C. Production of lentiviral vectors. Molecular Therapy—Methods and Clinical Development 3, 16017 (2016).

Pear, W. S., Nolan, G. P., Scott, M. L. and Baltimore, D. Production of high-titer helper-free retroviruses by transient transfection. Proceedings of the National Academy of Sciences 90, 8392-8396 (1993).

Dalby, B. et al. Advanced transfection with Lipofectamine 2000 reagent: primary neurons, siRNA, and high-throughput applications. Methods 33, 95-103 (2004).

Boussif, O. et al. A versatile vector for gene and oligonucleotide transfer into cells in culture and in vivo: polyethylenimine. Proceedings of the National Academy of Sciences 92, 7297-7301 (1995).

Mislick, K. A. and Baldeschwieler, J. D. Evidence for the role of proteoglycans in cation-mediated gene transfer. Proceedings of the National Academy of Sciences 93, 12349-12354 (1996).

Rejman, J., Bragonzi, A. and Conese, M. Role of clathrin- and caveolae-mediated endocytosis in gene transfer mediated by lipo- and polyplexes. Molecular Therapy 12, 468-474 (2005).

Bus, T., Traeger, A. and Schubert, U. S. The great escape: how cationic polyplexes overcome the endosomal barrier. Journal of Materials Chemistry B 6, 6904-6918 (2018).

Pollard, H. et al. Polyethylenimine but Not Cationic Lipids Promotes Transgene Delivery to the Nucleus in Mammalian Cells. Journal of Biological Chemistry 273, 7507-7511 (1998).

van der Loo, J. C. M. and Wright, J. F. Progress and challenges in viral vector manufacturing. Human Molecular Genetics 25, R42-R52 (2015).

Santos, J. L. et al. Continuous Production of Discrete Plasmid DNA-Polycation Nanoparticles Using Flash Nanocomplexation. Small 12, 6214-6222 (2016).

Hu, Y. et al. Kinetic Control in Assembly of Plasmid DNA/Polycation Complex Nanoparticles. ACS Nano 13, 10161-10178 (2019).

Ogris, M. et al. The size of DNA/transferrin-PEI complexes is an important factor for gene expression in cultured cells. Gene Therapy 5, 1425-1433 (1998).

Zhang, W. et al. Nano-Structural Effects on Gene Transfection: Large, Botryoid-Shaped Nanoparticles Enhance DNA Delivery via Macropinocytosis and Effective Dissociation. Theranostics 9, 1580-1598 (2019).

Tockary, T. A. et al. Single-Stranded DNA-Packaged Polyplex Micelle as Adeno-Associated-Virus-Inspired Compact Vector to Systemically Target Stroma-Rich Pancreatic Cancer. ACS Nano 13, 12732-12742 (2019).

Osada, K. et al. Quantized Folding of Plasmid DNA Condensed with Block Catiomer into Characteristic Rod Structures Promoting Transgene Efficacy. Journal of the American Chemical Society 132, 12343-12348 (2010).

Curtis, K. A. et al. Unusual Salt and pH Induced Changes in Polyethylenimine Solutions. PLOS ONE 11, e0158147 (2016).

Bertschinger, M. et al. Disassembly of polyethylenimine-DNA particles in vitro: Implications for polyethylenimine-mediated DNA delivery. Journal of Controlled Release 116, 96-104 (2006).

Johnson, B. K. and Prud'homme, R. K. Chemical processing and micromixing in confined impinging jets. AIChE Journal 49, 2264-2282 (2003).

Hao, Y., Seo, J.-H., Hu, Y., Mao, H.-Q. and Mittal, R. Flow physics and mixing quality in a confined impinging jet mixer. AIP Advances 10, 045105 (2020).

Bertschinger, M., Chaboche, S., Jordan, M. and Wurm, F. M. A spectrophotometric assay for the quantification of polyethylenimine in DNA nanoparticles. Analytical Biochemistry 334, 196-198 (2004).

Lächelt, U. and Wagner, E. Nucleic Acid Therapeutics Using Polyplexes: A Journey of 50 Years (and Beyond). Chemical Reviews 115, 11043-11078 (2015).

Thurston, T. L. M., Wandel, M. P., von Muhlinen, N., Foeglein, Á. and Randow, F. Galectin 8 targets damaged vesicles for autophagy to defend cells against bacterial invasion. Nature 482, 414-418 (2012).

Kilchrist, K. V. et al. Gal8 Visualization of Endosome Disruption Predicts Carrier-Mediated Biologic Drug Intracellular Bioavailability. ACS Nano 13, 1136-1152 (2019).

Rui, Y. et al. Carboxylated branched poly(β-amino ester) nanoparticles enable robust cytosolic protein delivery and CRISPR-Cas9 gene editing. Science Advances 5, eaay3255 (2019).

Rejman, J., Oberle, V., Zuhorn, I. S. and Hoekstra, D. Size-dependent internalization of particles via the pathways of clathrin- and caveolae-mediated endocytosis. Biochemical Journal 377, 159-169 (2004).

Mayor, S. and Pagano, R. E. Pathways of clathrin-independent endocytosis. Nature Reviews Molecular Cell Biology 8, 603-612 (2007).

Kopatz, I., Remy, J.-S. and Behr, J.-P. A model for non-viral gene delivery: through syndecan adhesion molecules and powered by actin. The Journal of Gene Medicine 6, 769-776 (2004).

Wilson, D. R. et al. A Triple-Fluorophore-Labeled Nucleic Acid pH Nanosensor to Investigate Non-viral Gene Delivery. Molecular Therapy 25, 1697-1709 (2017).

Karlsson, J., Rhodes, K. R., Green, J. J. and Tzeng, S. Y. Poly(beta-amino ester)s as gene delivery vehicles: challenges and opportunities. Expert Opinion on Drug Delivery 17, 1395-1410 (2020).

Yue, Y. et al. Revisit complexation between DNA and polyethylenimine—Effect of uncomplexed chains free in the solution mixture on gene transfection. Journal of Controlled Release 155, 67-76 (2011).

Ohi, M., Li, Y., Cheng, Y. and Walz, T. Negative staining and image classification—powerful tools in modern electron microscopy. Biological Procedures Online 6, 23-34 (2004).

Williford, J.-M. et al. Critical Length of PEG Grafts on 1PEI/DNA Nanoparticles for Efficient in Vivo Delivery. ACS Biomaterials Science and Engineering 2, 567-578 (2016).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for preparing a plurality of polycationic/nucleic acid nanoparticles, the method comprising:

(a) flowing a first stream comprising one or more water-soluble polycationic polymers at a first variable flow rate and a second stream comprising one or more nucleic acids at a second variable flow rate into a first flash nanocomplexation (FNC) mixer to form a plurality of nanoparticles having a first particle size;

(b) flowing a third stream comprising the plurality of nanoparticles having a first particle size at a third variable flow rate and a fourth stream comprising an assembly buffer at a fourth variable flow rate into a second FNC mixer to form a plurality of assembled nanoparticles;

(c) incubating the plurality of assembled nanoparticles formed in step (b) for a period of time to form a plurality of assembled nanoparticles having a second particle size; and (d) flowing a fifth stream comprising the plurality of assembled nanoparticles having a second particle size at a fifth variable flow rate and a sixth stream comprising a stabilization buffer at a sixth variable flow rate into a third FNC mixer to form a plurality of polycationic/nucleic acid nanoparticles.

2. The method of claim 1, wherein the one or more water-soluble polycationic polymers are selected from the group consisting of polyethylenimine (PEI), chitosan, PAMAM dendrimers, protamine, poly(arginine), poly(lysine), poly(beta-aminoesters), cationic peptides and derivatives thereof.

3. The method of claim 1, wherein the first stream comprising one or more water-soluble polycationic polymers has a concentration of polyethylenimine ranging from about 0.04 mg/mL to 3 mg/mL.

4. The method of claim 1, wherein the one or more nucleic acids are selected from the group consisting of an antisense oligonucleotide, cDNA, genomic DNA, guide RNA, plasmid DNA, vector DNA, mRNA, miRNA, piRNA, shRNA, siRNA, and a mixture of one or more plasmid DNAs.

5. The method of 4, wherein the one or more nucleic acids comprise a mixture one or more plasmid DNAs, wherein the one or more plasmid DNAs comprise a transfer plasmid and plasmid DNAs encoding a gag protein, a pol protein, a rev protein, and an env protein.

6. The method of claim 5, wherein the transfer plasmid encodes a lentiviral vector.

7. The method of claim 6, wherein the lentiviral vector comprises a modified left (5') lentiviral LTR comprising a heterologous promoter, a Psi packaging sequence (Ψ+), a cPPT/FLAP, an RRE, a promoter operably linked to a polynucleotide encoding a therapeutic transgene, and a modified SIN (3') lentiviral LTR.

8. The method of claim 5, wherein the env protein comprises a VSV-g envelope glycoprotein.

9. The method of claim 1, wherein the second stream comprising one or more nucleic acids has a DNA concentration ranging from about 20 μg/mL to 800 μg/mL.

10. The method of claim 1, wherein the first variable flow rate, the second variable flow rate, the third variable flow rate, the fourth variable flow rate, the fifth variable flow rate, and the sixth variable flow rate are each independently between about 5 mL/min to about 400 mL/min.

11. The method of claim 1, wherein the plurality of nanoparticles having a first particle size are formed under conditions at a pH of about 2.0 to 4.0 and a conductivity of about 0.05 to 0.8 mS $cm^{-1}$.

12. The method of claim 1, wherein the first particle size has a range between about 40 nm to about 120 nm and the second particle size has a range between about 300 nm to about 500 nm.

13. The method of claim 1, wherein the assembly buffer comprises phosphate buffered saline comprising one or more of NaCl, KCl, $Na_2HPO_4$, $KH_2PO_4$, and combinations thereof, and/or has a pH from about 6.0 to about 8.0 and a conductivity of about 2.0 to 25.0 mS $cm^{-1}$.

14. The method of claim 1, wherein the plurality of nanoparticles formed in step (b) are incubated at about room temperature (22±4° C.) for a period of time, wherein the period of time ranges from about 0.2 to about 5 hours.

15. The method of claim 1, wherein the plurality of polycationic/nucleic acid nanoparticles of step (d) are formed in a stabilization buffer at a pH of about 2.0 to 4.0, and a conductivity of about 1.0 to 15.0 mS $cm^{-1}$, wherein the stabilization buffer optionally comprises one or more sugars, wherein the one or more sugars comprise between about 10% to about 30% w/w trehalose.

16. The method of claim 1, further comprising lyophilizing or freezing the particles at about −80° C. for storage.

* * * * *